(12) United States Patent
Fink et al.

(10) Patent No.: US 7,677,467 B2
(45) Date of Patent: Mar. 16, 2010

(54) METHODS AND DEVICES FOR AEROSOLIZING MEDICAMENT

(75) Inventors: James B. Fink, San Mateo, CA (US); Nicanor A. Domingo, Santa Clara, CA (US)

(73) Assignee: Novartis Pharma AG, Basel (CH)

( * ) Notice: Subject to any disclaimer, the term of this patent is extended or adjusted under 35 U.S.C. 154(b) by 526 days.

(21) Appl. No.: 11/111,492

(22) Filed: Apr. 20, 2005

(65) Prior Publication Data

US 2005/0199236 A1    Sep. 15, 2005

Related U.S. Application Data

(63) Continuation-in-part of application No. 11/039,709, filed on Jan. 19, 2005, now abandoned, which is a continuation-in-part of application No. 10/043,075, filed on Jan. 7, 2002, now Pat. No. 6,851,626.

(51) Int. Cl.
*A62C 35/00* (2006.01)
(52) U.S. Cl. .................. 239/8; 239/365; 239/370; 239/317; 239/338; 239/419.5; 239/425.5; 128/200.23; 128/200.16; 128/200.18
(58) Field of Classification Search ................. 239/372, 239/370, 419.5, 425.5; 128/203.15, 200.14, 128/200.16, 200.18, 200.21, 200.23
See application file for complete search history.

(56) References Cited

U.S. PATENT DOCUMENTS

| 550,315 | A | 11/1895 | Allen |
|---|---|---|---|
| 809,159 | A | 1/1906 | Willis et al. |
| 1,680,616 | A | 8/1928 | Horst |
| 2,022,520 | A | 11/1935 | Philbrick |
| 2,101,304 | A | 12/1937 | Wright |
| 2,158,615 | A | 5/1939 | Wright |
| 2,187,528 | A | 1/1940 | Wing |
| 2,223,541 | A | 12/1940 | Baker |

(Continued)

FOREIGN PATENT DOCUMENTS

CH    477 865    9/1969

(Continued)

OTHER PUBLICATIONS

Heyder, J. et al., "Deposition of particles in the human respiratory tract in the size range 0.005-15 microns." J Aerosol Sci 17: 811-825, 1986.

(Continued)

*Primary Examiner*—Dinh Q Nguyen
(74) *Attorney, Agent, or Firm*—Michael J. Mazza (57) ABSTRACT

Methods and devices are provided for aerosolizing medicament to be inhaled by a user. A housing is provided with an aerosol generator contained within the housing. A medicament feed system supplies medicament to the aerosol generator. A mouthpiece has separate medicament and air flow passages. The medicament flow passage provides aerosolized medicament from the aerosol generator to an outlet of the medicament flow passage, and the air flow passage has an inlet in fluid communication with an ambient atmosphere. The outlets of the medicament and air flow passages are provided at an end of the mouthpiece to provide simultaneous flows of medicament and air that mix in the user's mouth upon inhalation by the user at the end of the mouthpiece.

20 Claims, 9 Drawing Sheets

U.S. PATENT DOCUMENTS

| | | | |
|---|---|---|---|
| 2,266,706 A | 12/1941 | Fox et al. | |
| 2,283,333 A | 5/1942 | Martin | |
| 2,292,381 A | 8/1942 | Klagges | |
| 2,360,297 A | 10/1944 | Wing | |
| 2,375,770 A | 5/1945 | Dahlberg | |
| 2,383,098 A | 8/1945 | Wheaton | |
| 2,404,063 A | 7/1946 | Healy | |
| 2,430,023 A | 11/1947 | Longmaid | |
| 2,474,996 A | 7/1949 | Wallis | |
| 2,512,004 A | 6/1950 | Wing | |
| 2,521,657 A | 9/1950 | Severy | |
| 2,681,041 A | 6/1954 | Zodtner et al. | |
| 2,705,007 A | 3/1955 | Gerber | |
| 2,735,427 A | 2/1956 | Sullivan | |
| 2,764,946 A | 10/1956 | Henderson | |
| 2,764,979 A | 10/1956 | Henderson | |
| 2,779,623 A | 1/1957 | Eisenkraft | |
| 2,935,970 A | 5/1960 | Morse et al. | |
| 3,103,310 A | 9/1963 | Lang | |
| 3,325,031 A | 6/1967 | Singier | |
| 3,411,854 A | 11/1968 | Roster et al. | |
| 3,515,348 A | 6/1970 | Coffman, Jr. | |
| 3,550,864 A | 12/1970 | East | |
| 3,558,052 A | 1/1971 | Dunn | |
| 3,561,444 A | 2/1971 | Boucher | |
| 3,563,415 A | 2/1971 | Ogle | |
| 3,680,954 A | 8/1972 | Frank | |
| 3,719,328 A | 3/1973 | Hindman | |
| 3,738,574 A | 6/1973 | Guntersdorfer et al. | |
| 3,771,982 A | 11/1973 | Dobo | |
| 3,790,079 A | 2/1974 | Berglund et al. | |
| 3,804,329 A | 4/1974 | Martner | |
| 3,812,854 A * | 5/1974 | Michaels et al. | 128/200.16 |
| 3,838,686 A | 10/1974 | Szekely | |
| 3,842,833 A | 10/1974 | Ogle | |
| 3,865,106 A | 2/1975 | Palush | |
| 3,903,884 A | 9/1975 | Huston et al. | |
| 3,906,950 A | 9/1975 | Cocozza | |
| 3,908,654 A | 9/1975 | Lhoest et al. | |
| 3,950,760 A | 4/1976 | Rauch et al. | |
| 3,951,313 A | 4/1976 | Coniglione | |
| 3,958,249 A | 5/1976 | DeMaine et al. | |
| 3,970,250 A | 7/1976 | Drews | |
| 3,983,740 A | 10/1976 | Danel | |
| 3,993,223 A | 11/1976 | Welker, III et al. | |
| 4,005,435 A | 1/1977 | Lundquist et al. | |
| 4,030,492 A | 6/1977 | Simbruner | |
| 4,052,986 A | 10/1977 | Scaife | |
| 4,059,384 A | 11/1977 | Holland et al. | |
| D246,574 S | 12/1977 | Meierhoefer | |
| 4,076,021 A | 2/1978 | Thompson | |
| 4,083,368 A | 4/1978 | Freezer | |
| 4,094,317 A | 6/1978 | Wasnich | |
| 4,101,041 A | 7/1978 | Mauro, Jr. et al. | |
| 4,106,503 A | 8/1978 | Rosenthal et al. | |
| 4,109,174 A | 8/1978 | Hodgson | |
| 4,113,809 A | 9/1978 | Abair et al. | |
| D249,958 S | 10/1978 | Meierhoefer | |
| 4,119,096 A | 10/1978 | Drews | |
| 4,121,583 A | 10/1978 | Chen | |
| 4,159,803 A | 7/1979 | Cameto et al. | |
| 4,207,990 A | 6/1980 | Weiler et al. | |
| 4,210,155 A | 7/1980 | Grimes | |
| 4,226,236 A | 10/1980 | Genese | |
| 4,240,081 A | 12/1980 | Devitt | |
| 4,240,417 A | 12/1980 | Holever | |
| 4,248,227 A | 2/1981 | Thomas | |
| 4,261,512 A | 4/1981 | Zierenberg | |
| D259,213 S | 5/1981 | Pagels | |
| 4,268,460 A | 5/1981 | Boiarski et al. | |
| 4,294,407 A | 10/1981 | Reichl et al. | |
| 4,298,045 A | 11/1981 | Weiler et al. | |
| 4,299,784 A | 11/1981 | Hense | |
| 4,300,546 A | 11/1981 | Kruber | |
| 4,301,093 A | 11/1981 | Eck | |
| 4,319,155 A | 3/1982 | Makai et al. | |
| 4,334,531 A | 6/1982 | Reichl et al. | |
| 4,336,544 A | 6/1982 | Donald et al. | |
| 4,338,576 A | 7/1982 | Takahashi et al. | |
| 4,368,476 A | 1/1983 | Uehara et al. | |
| 4,368,850 A | 1/1983 | Szekely | |
| 4,374,707 A | 2/1983 | Pollack | |
| 4,389,071 A | 6/1983 | Johnson, Jr. et al. | |
| 4,408,719 A | 10/1983 | Last | |
| 4,428,802 A | 1/1984 | Kanai et al. | |
| 4,431,136 A | 2/1984 | Janner et al. | |
| 4,454,877 A | 6/1984 | Miller et al. | |
| 4,465,234 A | 8/1984 | Maehara et al. | |
| 4,474,251 A | 10/1984 | Johnson, Jr. | |
| 4,474,326 A | 10/1984 | Takahashi | |
| 4,475,113 A | 10/1984 | Lee et al. | |
| 4,479,609 A | 10/1984 | Maeda et al. | |
| 4,512,341 A | 4/1985 | Lester | |
| 4,530,464 A | 7/1985 | Yamamoto et al. | |
| 4,533,082 A | 8/1985 | Maehara et al. | |
| 4,539,575 A | 9/1985 | Nilsson | |
| 4,544,933 A | 10/1985 | Heinzl | |
| 4,546,361 A | 10/1985 | Brescia et al. | |
| 4,550,325 A | 10/1985 | Viola | |
| 4,566,452 A | 1/1986 | Farr | |
| 4,591,883 A | 5/1986 | Isayama | |
| 4,593,291 A | 6/1986 | Howkins | |
| 4,605,167 A | 8/1986 | Maehara | |
| 4,613,326 A | 9/1986 | Szwarc | |
| 4,620,201 A | 10/1986 | Heinzl et al. | |
| 4,628,890 A | 12/1986 | Freeman | |
| 4,632,311 A | 12/1986 | Nakane et al. | |
| 4,658,269 A | 4/1987 | Rezanka | |
| 4,659,014 A | 4/1987 | Soth et al. | |
| 4,677,975 A | 7/1987 | Edgar et al. | |
| 4,678,680 A | 7/1987 | Abowitz | |
| 4,679,551 A | 7/1987 | Anthony | |
| 4,681,264 A | 7/1987 | Johnson, Jr. | |
| 4,693,853 A | 9/1987 | Falb et al. | |
| 4,702,418 A | 10/1987 | Carter et al. | |
| 4,722,906 A | 2/1988 | Guire | |
| 4,753,579 A | 6/1988 | Murphy | |
| 4,790,479 A | 12/1988 | Matsumoto et al. | |
| 4,793,339 A | 12/1988 | Matsumoto et al. | |
| 4,796,807 A | 1/1989 | Bendig et al. | |
| 4,799,622 A | 1/1989 | Ishikawa et al. | |
| 4,805,609 A | 2/1989 | Roberts et al. | |
| 4,819,629 A | 4/1989 | Jonson | |
| 4,819,834 A | 4/1989 | Thiel | |
| 4,826,080 A | 5/1989 | Ganser | |
| 4,826,759 A | 5/1989 | Guire et al. | |
| 4,828,886 A | 5/1989 | Hieber | |
| 4,843,445 A | 6/1989 | Stemme | |
| 4,849,303 A | 7/1989 | Graham et al. | |
| 4,850,534 A | 7/1989 | Takahashi et al. | |
| 4,865,006 A | 9/1989 | Nogi et al. | |
| 4,871,489 A | 10/1989 | Ketcham | |
| 4,872,553 A | 10/1989 | Suzuki et al. | |
| 4,877,989 A | 10/1989 | Drews et al. | |
| 4,888,516 A | 12/1989 | Daeges et al. | |
| 4,922,901 A | 5/1990 | Brooks et al. | |
| 4,926,915 A | 5/1990 | Deussen et al. | |
| 4,934,358 A | 6/1990 | Nilsson et al. | |
| 4,954,225 A | 9/1990 | Bakewell | |
| 4,957,239 A | 9/1990 | Tempelman | |
| 4,964,521 A | 10/1990 | Wieland et al. | |
| D312,209 S | 11/1990 | Morrow et al. | |
| 4,968,299 A | 11/1990 | Ahlstrand et al. | |
| 4,971,665 A | 11/1990 | Sexton | |

| | | | | | | |
|---|---|---|---|---|---|---|
| 4,973,493 A | 11/1990 | Guire | | 5,414,075 A | 5/1995 | Swan et al. |
| 4,976,259 A | 12/1990 | Higson et al. | | 5,415,161 A | 5/1995 | Ryder |
| 4,979,959 A | 12/1990 | Guire | | 5,419,315 A | 5/1995 | Rubsamen |
| 4,994,043 A | 2/1991 | Ysebaert | | 5,426,458 A | 6/1995 | Wenzel et al. |
| 5,002,048 A | 3/1991 | Makiej, Jr. | | 5,431,155 A | 7/1995 | Marelli |
| 5,002,582 A | 3/1991 | Guire et al. | | 5,435,282 A * | 7/1995 | Haber et al. ............ 128/200.16 |
| 5,007,419 A | 4/1991 | Weinstein et al. | | 5,435,297 A | 7/1995 | Klein |
| 5,016,024 A | 5/1991 | Lam et al. | | 5,437,267 A | 8/1995 | Weinstein et al. |
| 5,021,701 A | 6/1991 | Takahashi et al. | | 5,445,141 A | 8/1995 | Kee et al. |
| 5,022,587 A | 6/1991 | Hochstein | | D362,390 S | 9/1995 | Weiler |
| 5,024,733 A | 6/1991 | Abys et al. | | 5,449,502 A | 9/1995 | Igusa et al. |
| 5,046,627 A | 9/1991 | Hansen | | 5,452,711 A | 9/1995 | Gault |
| 5,062,419 A | 11/1991 | Rider | | 5,458,135 A | 10/1995 | Patton et al. |
| 5,063,396 A | 11/1991 | Shiokawa et al. | | 5,458,289 A | 10/1995 | Cater |
| 5,063,922 A | 11/1991 | Häkkinen | | 5,474,059 A | 12/1995 | Cooper |
| 5,073,484 A | 12/1991 | Swanson et al. | | 5,477,992 A | 12/1995 | Jinks et al. |
| 5,076,266 A | 12/1991 | Babaev | | 5,479,920 A | 1/1996 | Piper et al. |
| 5,080,093 A | 1/1992 | Raabe et al. | | 5,487,378 A | 1/1996 | Robertson et al. |
| 5,080,649 A | 1/1992 | Vetter | | 5,489,266 A | 2/1996 | Grimard |
| 5,086,765 A | 2/1992 | Levine | | 5,497,944 A | 3/1996 | Weston et al. |
| 5,086,785 A | 2/1992 | Gentile et al. | | D369,212 S | 4/1996 | Snell |
| 5,115,803 A | 5/1992 | Sioutas | | 5,511,726 A | 4/1996 | Greenspan et al. |
| 5,115,971 A | 5/1992 | Greenspan et al. | | 5,512,329 A | 4/1996 | Guire et al. |
| D327,008 S | 6/1992 | Friedman | | 5,512,474 A | 4/1996 | Clapper et al. |
| 5,122,116 A | 6/1992 | Kriesel et al. | | 5,515,841 A | 5/1996 | Robertson et al. |
| 5,129,579 A | 7/1992 | Conte | | 5,515,842 A | 5/1996 | Ramseyer et al. |
| 5,134,993 A | 8/1992 | Van Der Linden et al. | | 5,516,043 A | 5/1996 | Manna et al. |
| 5,139,016 A | 8/1992 | Waser | | 5,518,179 A | 5/1996 | Humberstone et al. |
| 5,140,740 A | 8/1992 | Weigelt | | 5,529,055 A | 6/1996 | Gueret |
| 5,147,073 A | 9/1992 | Cater | | 5,533,497 A | 7/1996 | Ryder |
| 5,152,456 A | 10/1992 | Ross et al. | | 5,542,410 A | 8/1996 | Goodman et al. |
| 5,157,372 A | 10/1992 | Langford | | 5,549,102 A | 8/1996 | Lintl et al. |
| 5,164,740 A | 11/1992 | Ivri | | 5,560,837 A | 10/1996 | Trueba |
| 5,169,029 A | 12/1992 | Behar et al. | | 5,563,056 A | 10/1996 | Swan et al. |
| 5,170,782 A | 12/1992 | Kocinski | | D375,352 S | 11/1996 | Bologna |
| 5,180,482 A | 1/1993 | Abys et al. | | 5,579,757 A | 12/1996 | McMahon et al. |
| 5,186,164 A | 2/1993 | Raghuprasad | | 5,582,330 A | 12/1996 | Iba |
| 5,186,166 A | 2/1993 | Riggs et al. | | 5,584,285 A | 12/1996 | Salter et al. |
| 5,198,157 A | 3/1993 | Bechet | | 5,586,550 A | 12/1996 | Ivri et al. |
| 5,201,322 A * | 4/1993 | Henry et al. ................. 600/532 | | 5,588,166 A | 12/1996 | Burnett |
| 5,213,860 A | 5/1993 | Laing | | 5,601,077 A | 2/1997 | Imbert |
| 5,217,148 A | 6/1993 | Cater | | 5,609,798 A | 3/1997 | Liu et al. |
| 5,217,492 A | 6/1993 | Guire et al. | | 5,632,878 A | 5/1997 | Kitano |
| 5,227,168 A | 7/1993 | Chvapil | | 5,635,096 A | 6/1997 | Singer et al. |
| 5,230,496 A | 7/1993 | Shillington et al. | | 5,637,460 A | 6/1997 | Swan et al. |
| 5,239,993 A * | 8/1993 | Evans .................... 128/203.15 | | 5,647,349 A | 7/1997 | Ohki et al. |
| 5,245,995 A | 9/1993 | Sullivan et al. | | 5,653,227 A | 8/1997 | Barnes et al. |
| 5,248,087 A | 9/1993 | Dressler | | 5,654,007 A | 8/1997 | Johnson et al. |
| 5,258,041 A | 11/1993 | Guire et al. | | 5,654,162 A | 8/1997 | Guire et al. |
| 5,261,601 A | 11/1993 | Ross et al. | | 5,654,460 A | 8/1997 | Rong |
| 5,263,992 A | 11/1993 | Guire | | 5,657,926 A | 8/1997 | Toda |
| 5,279,568 A | 1/1994 | Cater | | 5,660,166 A | 8/1997 | Lloyd |
| 5,297,734 A | 3/1994 | Toda | | 5,664,557 A | 9/1997 | Makiej, Jr. |
| 5,299,739 A | 4/1994 | Takahashi et al. | | 5,664,706 A | 9/1997 | Cater |
| 5,303,854 A | 4/1994 | Cater | | 5,665,068 A | 9/1997 | Takamura |
| 5,309,135 A | 5/1994 | Langford | | 5,666,946 A | 9/1997 | Langenback |
| 5,312,281 A | 5/1994 | Takahashi et al. | | 5,670,999 A | 9/1997 | Takeuchi et al. |
| 5,313,955 A | 5/1994 | Rodder | | 5,685,491 A | 11/1997 | Marks et al. |
| 5,319,971 A | 6/1994 | Osswald et al. | | 5,692,644 A | 12/1997 | Gueret |
| 5,320,603 A | 6/1994 | Vetter et al. | | 5,707,818 A | 1/1998 | Chudzik et al. |
| 5,322,057 A | 6/1994 | Raabe et al. | | 5,709,202 A | 1/1998 | Lloyd et al. |
| 5,342,011 A | 8/1994 | Short | | 5,714,360 A | 2/1998 | Swan et al. |
| 5,342,504 A | 8/1994 | Hirano et al. | | 5,714,551 A | 2/1998 | Bezwada et al. |
| 5,347,998 A | 9/1994 | Hodson et al. | | 5,718,222 A | 2/1998 | Lloyd et al. |
| 5,348,189 A | 9/1994 | Cater | | D392,184 S | 3/1998 | Weiler |
| 5,350,116 A | 9/1994 | Cater | | 5,724,957 A | 3/1998 | Rubsamen et al. |
| 5,355,872 A | 10/1994 | Riggs et al. | | 5,744,515 A | 4/1998 | Clapper |
| 5,357,946 A | 10/1994 | Kee et al. | | 5,752,502 A | 5/1998 | King |
| 5,372,126 A | 12/1994 | Blau | | 5,755,218 A | 5/1998 | Johansson et al. |
| 5,383,906 A | 1/1995 | Burchett et al. | | 5,758,637 A | 6/1998 | Ivri et al. |
| 5,388,571 A | 2/1995 | Roberts et al. | | 5,758,638 A * | 6/1998 | Kreamer ................ 128/200.23 |
| 5,392,768 A | 2/1995 | Johansson et al. | | 5,775,506 A | 7/1998 | Grabenkort |
| 5,396,883 A | 3/1995 | Knupp et al. | | 5,788,665 A | 8/1998 | Sekins |

| Patent No. | Date | Name |
|---|---|---|
| 5,788,819 A | 8/1998 | Onishi et al. |
| 5,790,151 A | 8/1998 | Mills |
| 5,810,004 A | 9/1998 | Ohki et al. |
| 5,819,730 A | 10/1998 | Stone et al. |
| 5,823,179 A | 10/1998 | Grychowski et al. |
| 5,823,428 A | 10/1998 | Humberstone et al. |
| 5,829,723 A | 11/1998 | Brunner et al. |
| 5,836,515 A | 11/1998 | Fonzes |
| 5,839,617 A | 11/1998 | Cater et al. |
| 5,842,468 A | 12/1998 | Denyer et al. |
| 5,862,802 A | 1/1999 | Bird |
| 5,865,171 A | 2/1999 | Cinquin |
| 5,878,900 A | 3/1999 | Hansen |
| 5,893,515 A | 4/1999 | Hahn et al. |
| 5,894,841 A | 4/1999 | Voges |
| 5,897,008 A | 4/1999 | Hansen |
| 5,910,698 A | 6/1999 | Yagi |
| 5,915,377 A | 6/1999 | Coffee |
| 5,918,637 A | 7/1999 | Fleischman |
| 5,925,019 A | 7/1999 | Ljungquist |
| 5,938,117 A | 8/1999 | Ivri |
| 5,950,619 A | 9/1999 | Van Der Linden et al. |
| 5,954,268 A | 9/1999 | Joshi et al. |
| 5,960,792 A | 10/1999 | Lloyd et al. |
| 5,964,417 A | 10/1999 | Amann et al. |
| 5,970,974 A | 10/1999 | Van Der Linden et al. |
| 5,976,344 A | 11/1999 | Abys et al. |
| 5,993,805 A | 11/1999 | Sutton et al. |
| 6,000,396 A | 12/1999 | Melker et al. |
| 6,007,518 A | 12/1999 | Kriesel et al. |
| 6,012,450 A | 1/2000 | Rubsamen |
| 6,014,970 A | 1/2000 | Ivri et al. |
| 6,026,809 A | 2/2000 | Abrams et al. |
| 6,029,666 A | 2/2000 | Aloy et al. |
| 6,032,665 A | 3/2000 | Psaros |
| 6,037,587 A | 3/2000 | Dowell et al. |
| 6,039,696 A | 3/2000 | Bell |
| 6,045,215 A | 4/2000 | Coulman |
| 6,045,874 A | 4/2000 | Himes |
| 6,047,818 A | 4/2000 | Warby et al. |
| 6,055,869 A | 5/2000 | Stemme et al. |
| 6,060,128 A | 5/2000 | Kim et al. |
| 6,062,212 A | 5/2000 | Davison et al. |
| 6,068,148 A | 5/2000 | Weiler |
| 6,085,740 A | 7/2000 | Ivri et al. |
| 6,096,011 A | 8/2000 | Trombley, III et al. |
| 6,105,877 A | 8/2000 | Coffee |
| 6,106,504 A | 8/2000 | Urrutia |
| 6,116,234 A | 9/2000 | Genova et al. |
| 6,123,413 A | 9/2000 | Agarwal et al. |
| 6,139,674 A | 10/2000 | Markham et al. |
| 6,142,146 A | 11/2000 | Abrams et al. |
| 6,145,963 A | 11/2000 | Pidwerbecki et al. |
| 6,146,915 A | 11/2000 | Pidwerbecki et al. |
| 6,152,130 A | 11/2000 | Abrams et al. |
| 6,155,676 A | 12/2000 | Etheridge et al. |
| 6,158,431 A | 12/2000 | Poole |
| 6,161,536 A | 12/2000 | Redmon et al. |
| 6,163,588 A | 12/2000 | Matsumoto et al. |
| 6,182,662 B1 | 2/2001 | McGhee |
| 6,186,141 B1 | 2/2001 | Pike et al. |
| 6,196,218 B1 | 3/2001 | Voges |
| 6,196,219 B1 | 3/2001 | Hess et al. |
| 6,205,999 B1 | 3/2001 | Ivri et al. |
| 6,216,916 B1 | 4/2001 | Maddox et al. |
| 6,223,746 B1 | 5/2001 | Jewett et al. |
| 6,235,177 B1 | 5/2001 | Borland et al. |
| 6,254,219 B1 | 7/2001 | Agarwal et al. |
| 6,260,549 B1 * | 7/2001 | Sosiak .................. 128/200.23 |
| 6,269,810 B1 | 8/2001 | Brooker et al. |
| 6,270,473 B1 | 8/2001 | Schwebel |
| 6,273,342 B1 | 8/2001 | Terada et al. |
| 6,318,640 B1 | 11/2001 | Coffee |
| 6,328,030 B1 | 12/2001 | Kidwell et al. |
| 6,328,033 B1 | 12/2001 | Avrahami |
| 6,341,732 B1 | 1/2002 | Martin et al. |
| 6,358,058 B1 | 3/2002 | Strupat et al. |
| 6,394,363 B1 | 5/2002 | Arnott et al. |
| 6,402,046 B1 | 6/2002 | Loser |
| 6,405,934 B1 | 6/2002 | Hess et al. |
| 6,427,682 B1 | 8/2002 | Klimowicz et al. |
| 6,443,146 B1 | 9/2002 | Voges |
| 6,443,366 B1 | 9/2002 | Hirota et al. |
| 6,467,476 B1 | 10/2002 | Ivri et al. |
| 6,530,370 B1 | 3/2003 | Heinonen |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,581,595 B1 | 6/2003 | Murdock et al. |
| 6,615,824 B2 | 9/2003 | Power |
| 6,629,646 B1 | 10/2003 | Ivri |
| 6,640,804 B2 | 11/2003 | Ivri |
| 6,651,650 B1 | 11/2003 | Yamamoto et al. |
| 6,705,315 B2 | 3/2004 | Sullivan et al. |
| 6,732,944 B2 | 5/2004 | Litherland et al. |
| 6,745,768 B2 | 6/2004 | Colla et al. |
| 6,745,770 B2 | 6/2004 | McAuliffe et al. |
| 6,755,189 B2 | 6/2004 | Ivri et al. |
| 6,769,626 B1 | 8/2004 | Haveri |
| 6,782,886 B2 | 8/2004 | Narayan et al. |
| 6,810,876 B2 | 11/2004 | Berthon-Jones |
| 6,814,071 B2 | 11/2004 | Klimowicz et al. |
| 6,817,361 B2 | 11/2004 | Berthon-Jones et al. |
| 6,840,240 B1 | 1/2005 | Berthon-Jones et al. |
| 6,845,770 B2 | 1/2005 | Klimowicz et al. |
| 6,851,626 B2 | 2/2005 | Patel et al. |
| 6,860,268 B2 | 3/2005 | Bohn et al. |
| 2001/0013554 A1 | 8/2001 | Borland et al. |
| 2001/0015737 A1 | 8/2001 | Truninger et al. |
| 2002/0011247 A1 | 1/2002 | Ivri et al. |
| 2002/0023650 A1 | 2/2002 | Gunaratnam et al. |
| 2002/0033178 A1 | 3/2002 | Farrell et al. |
| 2002/0036601 A1 | 3/2002 | Puckeridge et al. |
| 2002/0078958 A1 | 6/2002 | Stenzler |
| 2002/0104530 A1 | 8/2002 | Ivri et al. |
| 2002/0121274 A1 | 9/2002 | Borland et al. |
| 2002/0134372 A1 | 9/2002 | Loeffler et al. |
| 2002/0134374 A1 | 9/2002 | Loeffler et al. |
| 2002/0134375 A1 | 9/2002 | Loeffler et al. |
| 2002/0134377 A1 | 9/2002 | Loeffler et al. |
| 2002/0162551 A1 | 11/2002 | Litherland |
| 2003/0140921 A1 | 7/2003 | Smith et al. |
| 2003/0145859 A1 | 8/2003 | Bohn et al. |
| 2003/0150445 A1 | 8/2003 | Power et al. |
| 2003/0150446 A1 | 8/2003 | Patel et al. |
| 2003/0226906 A1 | 12/2003 | Ivri |
| 2004/0000598 A1 | 1/2004 | Ivri |
| 2004/0004133 A1 | 1/2004 | Ivri et al. |
| 2004/0011358 A1 | 1/2004 | Smaldone et al. |
| 2004/0035413 A1 | 2/2004 | Smaldone et al. |
| 2004/0035490 A1 | 2/2004 | Power |
| 2004/0050947 A1 | 3/2004 | Power et al. |
| 2004/0139963 A1 | 7/2004 | Ivri et al. |
| 2004/0139968 A1 | 7/2004 | Loeffler et al. |
| 2004/0188534 A1 | 9/2004 | Litherland et al. |
| 2004/0194783 A1 | 10/2004 | McAuliffe et al. |
| 2004/0226561 A1 | 11/2004 | Colla et al. |
| 2004/0226566 A1 | 11/2004 | Gunaratnam et al. |
| 2004/0256488 A1 | 12/2004 | Loeffler et al. |
| 2005/0011514 A1 | 1/2005 | Power et al. |

| | | |
|---|---|---|
| 2005/0284469 A1 | 12/2005 | Tobia et al. |

FOREIGN PATENT DOCUMENTS

| | | |
|---|---|---|
| CH | 555 681 | 11/1974 |
| DE | 11 03 522 | 3/1961 |
| EP | 0 049 636 A1 | 4/1982 |
| EP | 0 103 161 A2 | 3/1984 |
| EP | 0 134 847 A1 | 3/1985 |
| EP | 0 178 925 A2 | 4/1986 |
| EP | 0 387 222 A1 | 9/1990 |
| EP | 0 432 992 A1 | 6/1991 |
| EP | 0 476 991 B1 | 3/1992 |
| EP | 0 480 615 A1 | 4/1992 |
| EP | 0 510 648 A2 | 10/1992 |
| EP | 0 516 565 A1 | 12/1992 |
| EP | 0 542 723 A2 | 5/1993 |
| EP | 0 933 138 A2 | 4/1999 |
| EP | 0 923 957 A1 | 6/1999 |
| EP | 1 142 600 A1 | 10/2001 |
| GB | 973 458 | 10/1964 |
| GB | 1 454 597 | 11/1976 |
| GB | 2 073 616 A | 10/1981 |
| GB | 2 101 500 | 1/1983 |
| GB | 2 177 623 A | 1/1987 |
| GB | 2 240 494 A | 7/1991 |
| GB | 2 272 389 A | 5/1994 |
| JP | 57-023852 | 2/1982 |
| JP | 57-105608 | 7/1982 |
| JP | 58-061857 | 4/1983 |
| JP | 58-139757 | 8/1983 |
| JP | 59-142163 A | 8/1984 |
| JP | 60-004714 | 1/1985 |
| JP | 61-008357 A | 1/1986 |
| JP | 61-215059 A | 9/1986 |
| JP | 02-135169 | 5/1990 |
| JP | 02-189161 | 7/1990 |
| JP | 60-07721 A | 1/1994 |
| WO | WO 82/03548 A | 10/1982 |
| WO | WO 92/07600 A1 | 5/1992 |
| WO | WO 92/11050 A1 | 9/1992 |
| WO | WO 92/17231 A1 | 10/1992 |
| WO | WO 93/01404 A1 | 1/1993 |
| WO | WO 93/10910 A1 | 6/1993 |
| WO | WO 94/09912 A1 | 5/1994 |
| WO | WO 96/09229 | 3/1996 |
| WO | WO 99/17888 | 4/1999 |
| WO | WO 00/37132 | 6/2000 |

OTHER PUBLICATIONS

Hickey, Anthony J. "Pharmaceutical Inhalation Aerosol Technology," Drugs And The Pharmaceutical Science, 1992, pp. 172-173, vol. 54.

Hikayama, H., et al. "Ultrasonic Atomizer with Pump Function" Tech. Rpt. IEICE Japan US88-74:25 (1988).

Jorch, G. Letter to the Editor, "Surfactant Aerosol Treatment of Respiratory Distress Syndrome in Spontaneously Breathing Premature Infants", Pediatric Pulmonology 24: 222-224, 1997, Wiley-Liss.

Maehara, N. et al. "Atomizing rate control of a multi-pinhole-plate ultrasonic atomizer" J. Acoustical Soc. Japan, 1988, pp. 116-121, 44:2.

Maehara, N. et al. "Influence of the vibrating system of a multipinhole-plate ultrasonic nebulizer on its performance" Review of Scientific Instruments, Nov. 1986, p. 2870-2876, vol. 57, No. 1.

Maehara, N. et al. "Influences of liquid's physical properties on the characteristics of a multi-pinhole-plate ultrasonic atomizer" J. Acoustical Soc. Japan 1988, pp. 425-431, 44:6.

Maehara, N. et al. "Optimum Design Procedure for Multi-Pinhole-Plate Ultrasonic Atomizer" Japanese Journal of Applied Physics, 1987, pp. 215-217, vol. 26, Supplement 26-1.

Nogi, T. et al. "Mixture Formation of Fuel Injection System in Gasoline Engine" Nippon Kikai Gakkai Zenkoku Taikai Koenkai Koen Ronbunshu 69:660-662 (1991).

Palla Tech Pd an Pd Alloy Processes—Procedure for the Analysis of Additive IVS in Palla Tech Plating Solutions by HPLC, Technical Bulletin, Electroplating Chemicals & Services, 029-A, Lucent Technologies,, pp. 1-5, 1996.

Siemens, "Servo Ultra Nebulizer 345 Operating Manual," pp. 1-23.

Smaldone, G. C. "Aerosolized Antibiotics: Current and Future", Respiratory Care, 2000, vol. 45, No. 6, pp. 667-675.

Smedsaas-Löfvenbert, A. "Nebulization of Drugs in a Nasal CPAP System", Scandinavian University Press, 1999, Acta Paediatr 88: 89-92, Sweden.

TSI Incorporated product catalog. Vibrating Orifice Aerosol Generator (1989).

Ueha, S., et al. "Mechanism of Ultrasonic Atomization Using a Multi-Pinhole Plate" J. Acoust. Soc. Jpn., 1985, pp. 21-26, (E)6, 1.

Wehl, Wolfgang R. "Ink-Jet Printing: The Present State of the Art" for Siemens AG, 1989.

Abys, J.A. et al., "Annealing Behavior of Palladium-Nickel Alloy Electrodeposits," Plating and Surface Finishing, Aug. 1996, pp. 1-7.

Allen, T. *Particle Size Measurement*, Third Edition, Chapman and Hall pp. 167-169 (1981).

Ashgriz, N. et al. "Development of a Controlled Spray Generator" Rev. Sci. Instrum., 1987, pp. 1291-1296, vol. 58, No. 7.

Berggren, E. "Pilot Study of Nebulized Surfactant Therapy for Neonatal Respiratory Distress Syndrome", Acta Paediatr 89: 460-464, Taylor & Francis, ISSN 0803-5253, 2000, Sweden.

Berglund, R.N., et al. "Generation of Monodisperse Aerosol Standards" Environ. Sci. Technology, Feb. 1973, pp. 147-153, vol. 7, No. 2.

Cipolla, D.C. et al., "Assessment of Aerosol Delivery Systems for Recombinant Human Deoxyribonuclease," S.T.P. Pharma Sciences 4(1) 50-62, 1994.

Cipolla, D.C. et al., "Characterization of Aerosols of Human Recombinant Deoxyribonuclease I (rhDNase) Generated by Neulizers," Pharmaceutical Research II (4) 491-498, 1994.

Dogan, Aydin PhD, Thesis: "Flexional 'Moonie and Cymbal' Actuators", Penn State University, 1994.

Duarte, Alexander G. et al. "Inhalation Therapy During Mechanical Ventilation" Respiratory Care Clinics of North America, Aerosol Therapy, Jun. 2001, pp. 233-259, vol. 7, No. 2.

Fink, James B. et al. "Aerosol Drug Therapy," Clinical Practice in Respiratory Care: Chapter 12, pp. 308-342; 1999.

Fink, James B. et al. "Aerosol Therapy in Mechanically Ventilated Patients: Recent Advances and New Techniques" Seminars in Respiratory and Critical Care Medicine, 2000, pp. 183-201, vol. 21, No. 3.

Fink, James B. et al. Diagram from and abstract of article entitled "Optimizing efficiency of nebulizers during mechanical ventilation: The effect of placement and type of ventilator circuit" Chest, Oct. 1999, 116:312S.

Gaiser Tool Company catalog, pp. 26, 29-30 (1990).

Gonda, I. "Therapeutic Aerosols," Pharmaceutics, The Science of Dosage Form Design, Editor: M.E. Aulton, 341-358, 1988.

Hancock, B.C. et al., "Molecular Mobility of Amorphous Pharmaceutical Solids Below Their Glass Transition Temperatures," Pharmaceutical Research 12, 799-806 (1995).

* cited by examiner

METHODS AND DEVICES FOR AEROSOLIZING MEDICAMENT

CROSS-REFERENCES TO RELATED APPLICATIONS

This application is a continuation-in-part of, and claims the benefit of the filing date of, U.S. patent application Ser. No. 11,039,709, entitled "METHODS AND DEVICES FOR AEROSOLIZING MEDICAMENT, filed Jan. 19, 2005, which is a continuation-in-part application of U.S. patent application Ser. No. 10/043,075, entitled "METHODS AND DEVICES FOR NEBULIZING FLUIDS," filed Jan. 7, 2002, the entire disclosure of which is incorporated herein by reference for all purposes.

BACKGROUND OF THE INVENTION

This application relates to generally methods and devices for aerosolizing medicament, as well as to methods and devices for storing and delivering medicament to be aerosolized. More specifically, this application relates to a mouthpiece for an unpressurized inhalation device.

One factor that influences the effectiveness of an inhalation device that has a mouthpiece and an aerosol generator is the percentage amount of aerosolized medicament emitted from the mouthpiece relative to the amount of medicament supplied to the aerosol generator. Typically, there is some loss of medicament caused by particle impaction, which results from the aerodynamic behavior of the particles carried by the inhalation medicament stream. In particular, the inhalation flow rate that passes through the mouthpiece of an inhalation device may range between about 15 and 60 liters/minute. This rate may cause flow within internal passages of the inhalation device to be turbulent, resulting in collision among aerosol particles and with internal surfaces of the mouthpiece. Consequently, some medicament remains in the mouthpiece and does not reach the lungs of the patient.

There is thus a general need in the art for methods and devices that improve the effectiveness of inhalation devices by reducing the amount of loss from such factors.

BRIEF SUMMARY OF THE INVENTION

Embodiments of the invention provide an aerosolizing device, which may be a hand-held aerosolizing device for inhalation of aerosolized medicament. The device has a mouthpiece through which a user inhales the aerosolized medicament. An aerosol generator may be provided as a vibrating element with holes through which the medicament is ejected, although other suitable aerosol generators may be used without departing from numerous aspects of the invention.

The medicament is held in a container that holds a number of doses of the medicament. The container delivers the medicament to a reservoir, which is designed to minimize the residual volume in the reservoir. An inner surface of the reservoir may be hydrophobic to encourage medicament to flow downward to the aerosol generator. The reservoir is may also be tear-drop shaped and have a smooth inner surface that is free of seams and corners to further encourage downward flow. The container and reservoir may be replaced independently or at the same time. The reservoir and container may also be formed as a single unit or may be separate units mounted to the device by the user.

The reservoir may also have a collection area located adjacent to the vibrating element where a final volume of medicament accumulates. The final volume is drawn over the holes in the vibrating element when the vibrating element is vibrated, thereby reducing the residual volume. The reservoir may also be designed so that the aerosol generator is positioned at a relatively low hydrostatic position when the device is positioned in a particular operating orientation. For example, the aerosol generator may be positioned so that less than 25%, and even less than 10%, of the volume of the reservoir is positioned below the aerosol generator.

The reservoir may also have one or more vent holes for smooth medicament delivery into the reservoir during filling and out of the reservoir when the medicament is being aerosolized. The vent holes may be sized to prevent the medicament from escaping therethrough.

The medicament path between the container and reservoir may include a valve that prevents contamination of the container and medicament path. The valve maintains the sterility of the container so that the container does not need to be pierced a number of times, as might otherwise be necessary. The valve may be positioned at a wall of the reservoir so that the valve isolates the entire medicament path together with the container.

Various aspects of the present invention are also directed to a container. The container is similar to a standard vial with the addition of a specialized connector. The connector mates with the aerosolizing device and, in another aspect, may mate with the reservoir as well. The connector has a protrusion that engages an L-shaped slot in the device for a bayonet-type connection. The connector also has a number of tabs or hooks that engage the reservoir to lock the reservoir to the container.

The mouthpiece may define separate medicament and air flow passages, each such passage having an outlet into the user's mouth when the device is used. The aerosol generator provides aerosolized medicament along the medicament flow passage, such as in response to inhalation by the user. The air flow passage has an inlet in communication with an ambient atmosphere so that air flows along the air flow passage, such as may also be in response to user inhalation. Separation of the medicament and air flows causes the medicament to be mixed with the air in the user's mouth, providing improved effectiveness of the device in delivering medicament. Greater than 90% of medicament provided to the aerosol generator may be expelled through the outlet of the medicament flow passage. In one embodiment, the outlet of the air flow passage is disposed substantially below the outlet of the medicament flow passage when the mouthpiece is oriented for insertion into the user's mouth.

The mouthpiece may be separable from the rest of the housing. The aerosol generator may also be contained within the mouthpiece so that the aerosol generator may be cleaned along with the mouthpiece. The mouthpiece may also have a port that receives a pressure-sensing conduit. The pressure-sensing conduit leads from the medicament flow passage to a pressure sensor. The pressure sensor is used for breath actuation of the device by sensing the drop in pressure when the user inhales on the mouthpiece.

These and other aspects of the invention are disclosed and described in the following description, drawings, and claims.

DETAILED DESCRIPTION OF THE INVENTION

Referring initially to FIGS. 1-8, an aerosolizing device 2 is shown. The aerosolizing device 2 may be a hand-held inhalation device, although various aspects of the invention may be practiced with any other aerosolizing device or inhalation device. The aerosolizing device 2 has a housing 4 that includes a mouthpiece 6 through which a user inhales an aerosolized medicament. In one embodiment, described in more detail in connection with FIGS. 9A and 9B below, the medicament is aerosolized by an aerosol generator 8 and mixed in a patient's mouth with air drawn through a separate air-flow passage. Embodiments of the invention are applicable both to liquid and powder medicaments, both of which may exhibit fluid behavior. In instances where the medicament comprises a liquid medicament, the aerosol generator 8 may comprise a nebulizing element.

The medicament to be aerosolized is stored in a container 12, such as a vial 15, which may hold a number of doses of the medicament. The container 12 is removed and replaced as necessary. The user selects a dose size or amount and delivers the dose from the container 12 to a reservoir 14, which holds the medicament. The reservoir 14 may be removed and replaced together with or separate from the container 12 as explained below.

Figure 1:
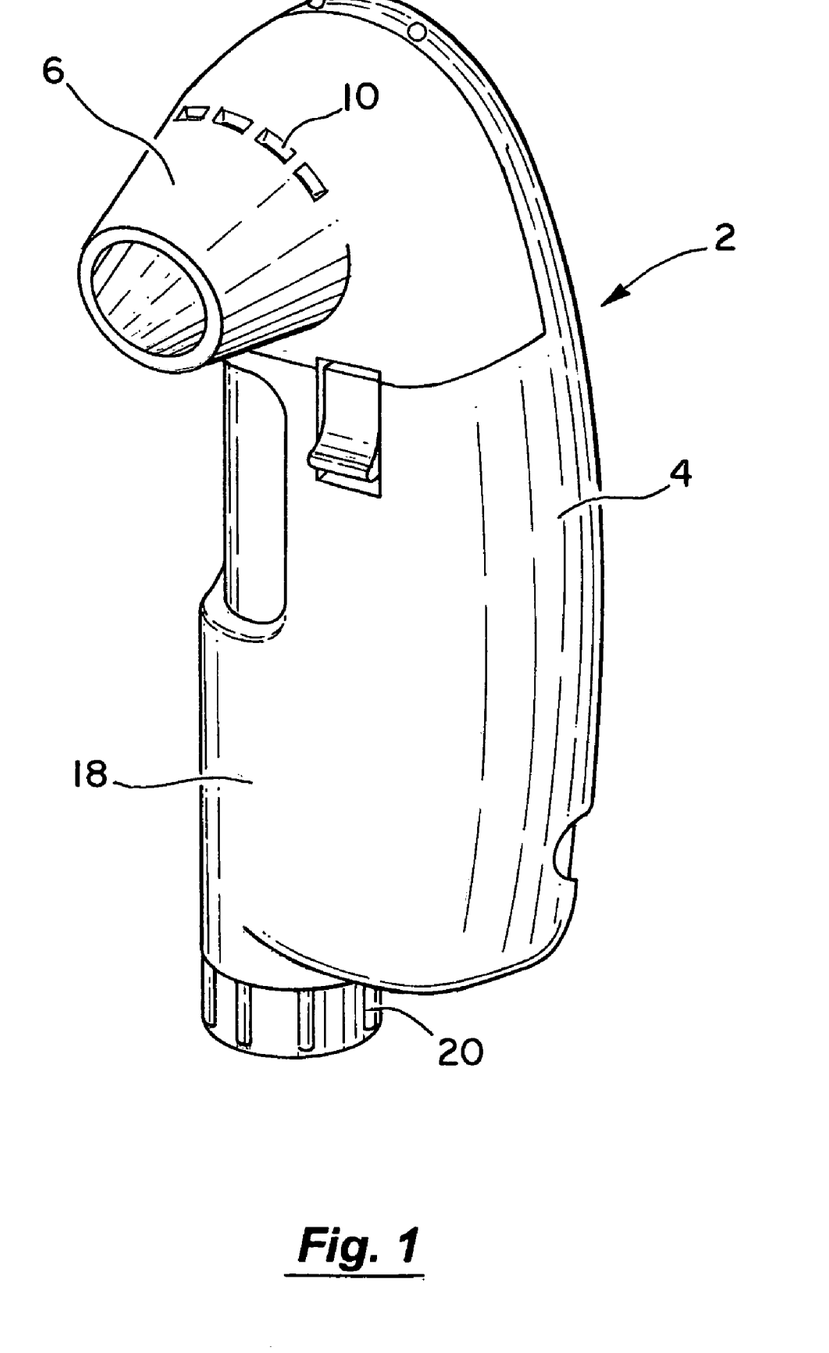
FIG. 1 shows an aerosolizing device.
Figure 2:
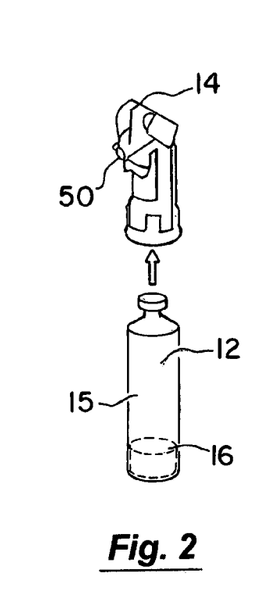
FIG. 2 shows a medicament assembly formed by a reservoir and a container.

The container 12 has a piston 16, which is moved by a dosing mechanism 18 to dispense a volume of the medicament. The dosing mechanism 18 may be any suitable dosing mechanism such as the dosing mechanisms for insulin pen mechanisms. The dosing mechanism 18 is operated with a dosing control 20 that the user operates to select and deliver a quantity of medicament to the reservoir 14. The housing 4 has a window to view the amount of medicament in the container 12.

Figure 3:
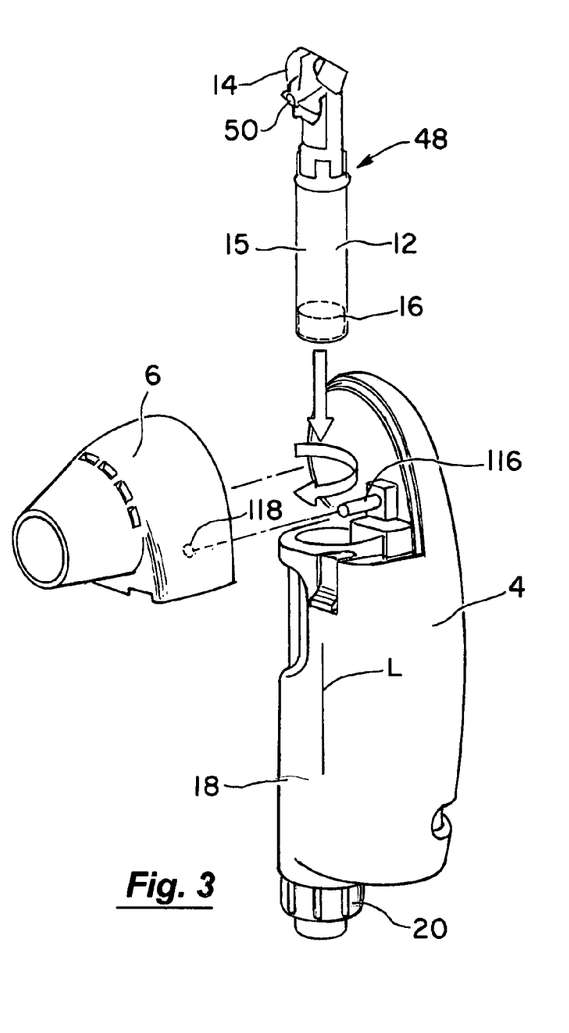
FIG. 3 shows the aerosolizing device with a mouthpiece and medicament assembly removed.
Figure 5:
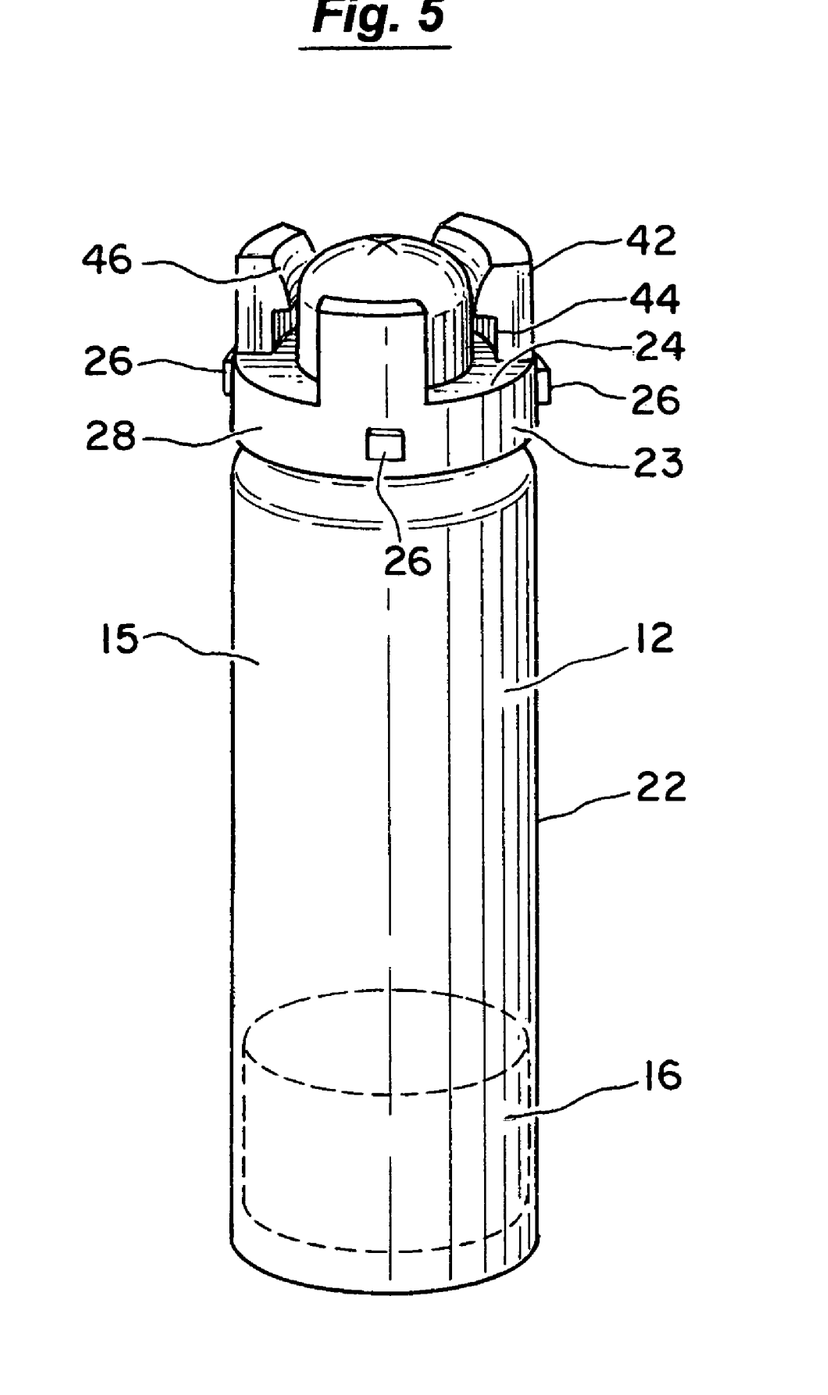
FIG. 5 shows the container.

The container 12 has a body 22 similar to a standard vial. The container 12 does differ from a standard vial in that the container 12 has a connector 23, such as a collar 24, which mates with the reservoir 14 and the aerosolizing device 2. To this end, the connector 23 has a bayonet-type connection with the aerosolizing device 2. The connector 23 has three projections 26 extending from a cylindrical body 28. The projections register and slide within L-shaped slots 30 in the aerosolizing device 2. The container 12 is loaded into the device 2 by pushing downward and then rotating the collar 24 to secure the collar 24, and therefore container 12, to the device 2. The slots 30 may have a raised portion or detent to lock the projection in the slot 30. The position, size, spacing, and orientation of the projections 26 and corresponding slots 30 may be altered for different medicaments to prevent use of an improper medicament. The device 2 may also have a sensor 32 that detects proper engagement of the projection 26 within the slot 30 before the device 2 will dispense medicament. The container 12 may, of course, have any suitable connection with the aerosolizing device 2 that helps to prevent use of an improper medicament.

Figure 6:
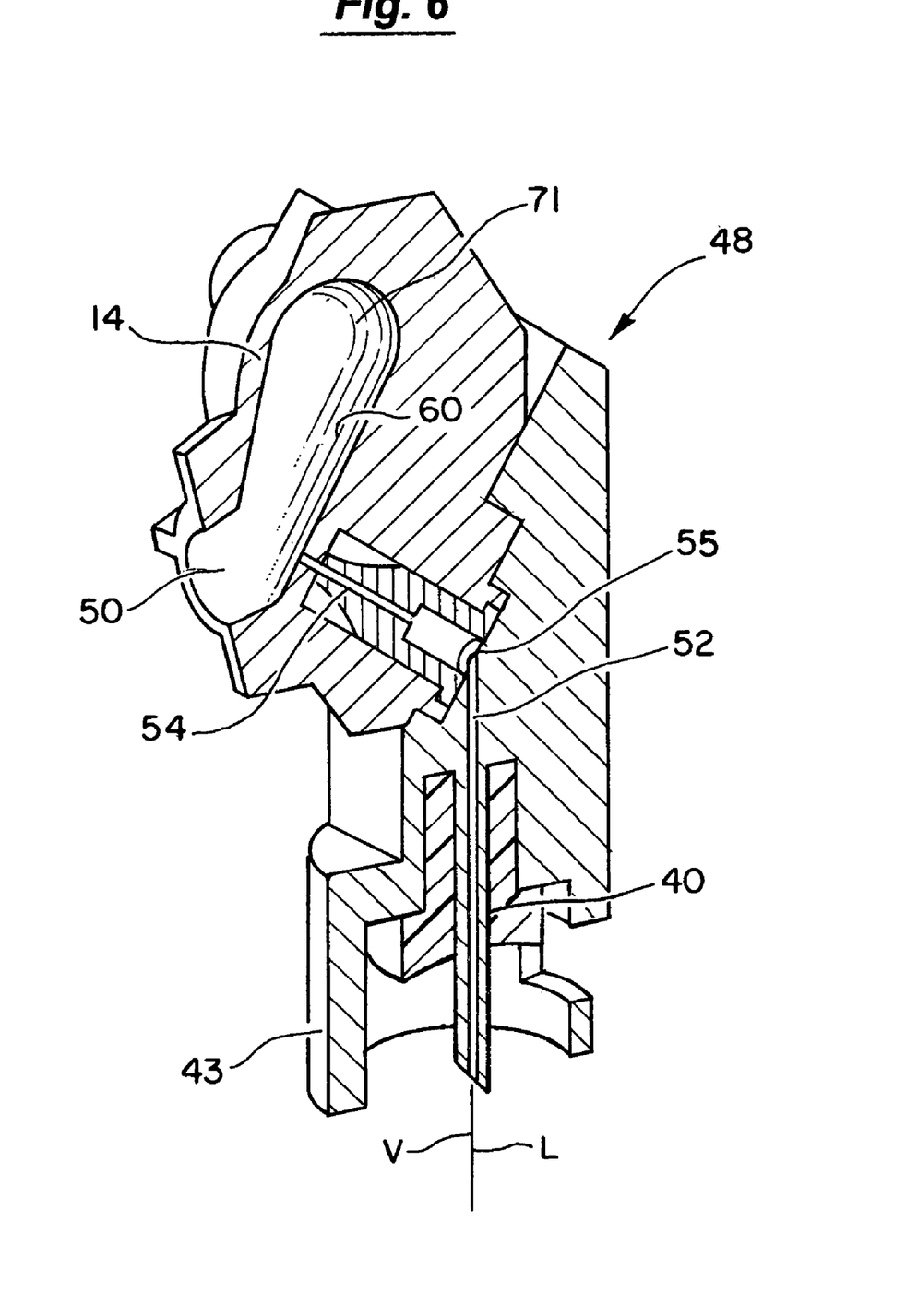
FIG. 6 is a perspective, cross-sectional view of the reservoir.
Figure 7:
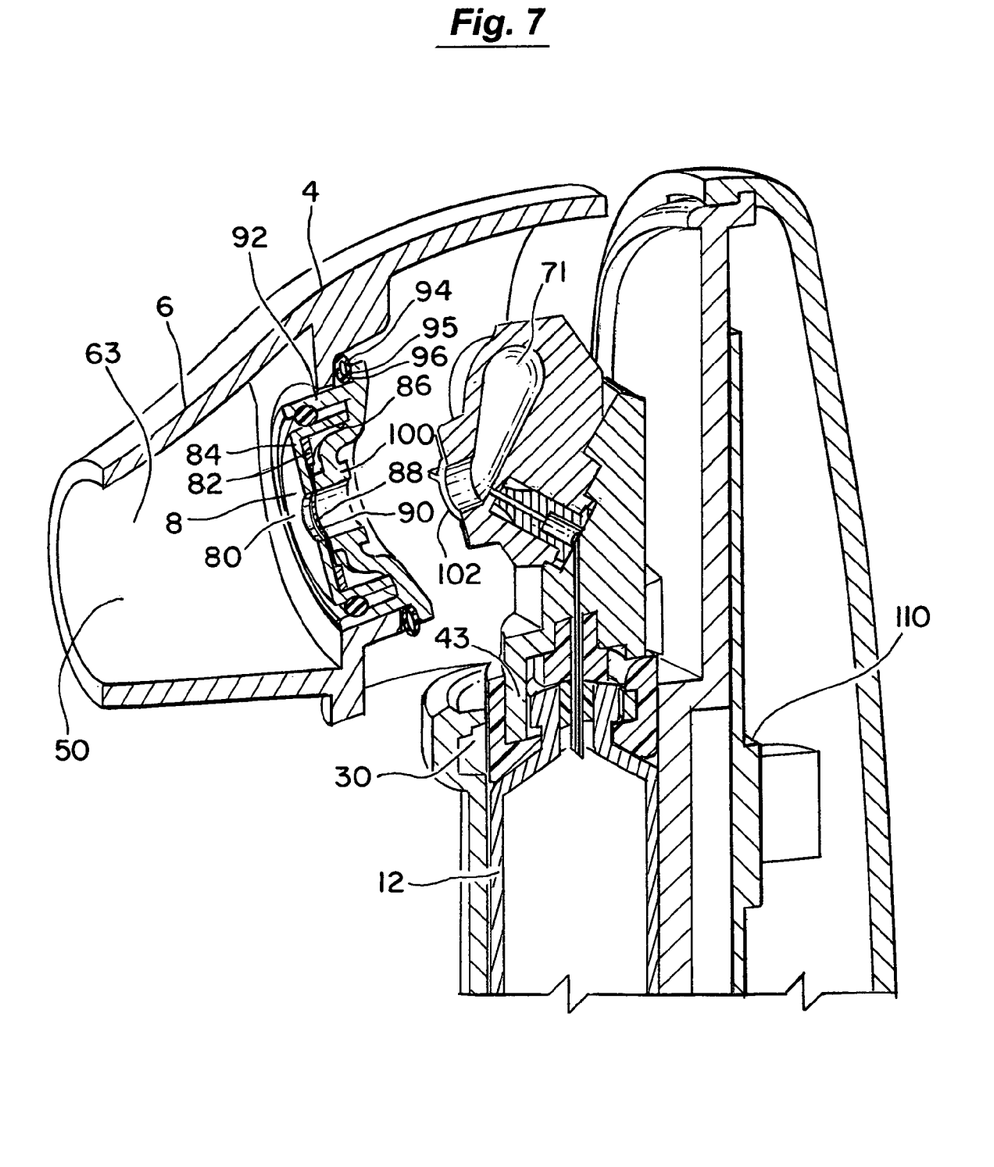
FIG. 7 is the perspective view of the device with the mouthpiece removed.
Figure 8:
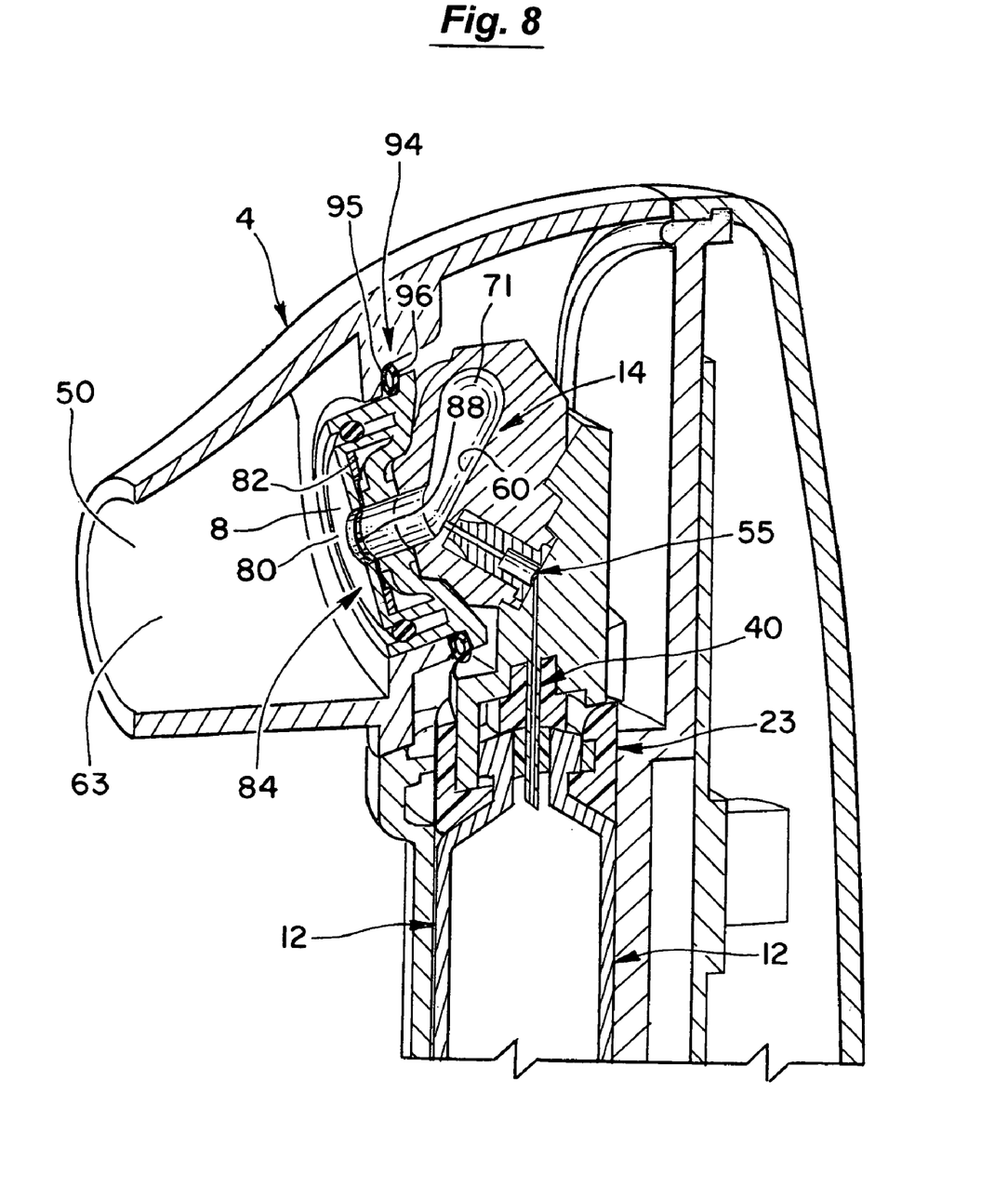
FIG. 8 is a perspective view corresponding to the view of FIG. 7 with the mouthpiece attached to the housing.

The container 12 also locks together with the reservoir 14 to provide a secure engagement with the reservoir 14. When the container 12 is mounted to the reservoir 14, a needle 40 pierces the container 12. The container 12 also has three tabs or hooks 42 that lock together with mating connectors on the reservoir 14. The tabs 42 are located about 120° apart and each have a recess 44 and a shoulder 46 that engages complementary features on a connector 43 on the reservoir 14. The container 12 and reservoir 14 may, of course, mount to one another in any other suitable manner and the features may be altered for different medicaments.

Figure 4:
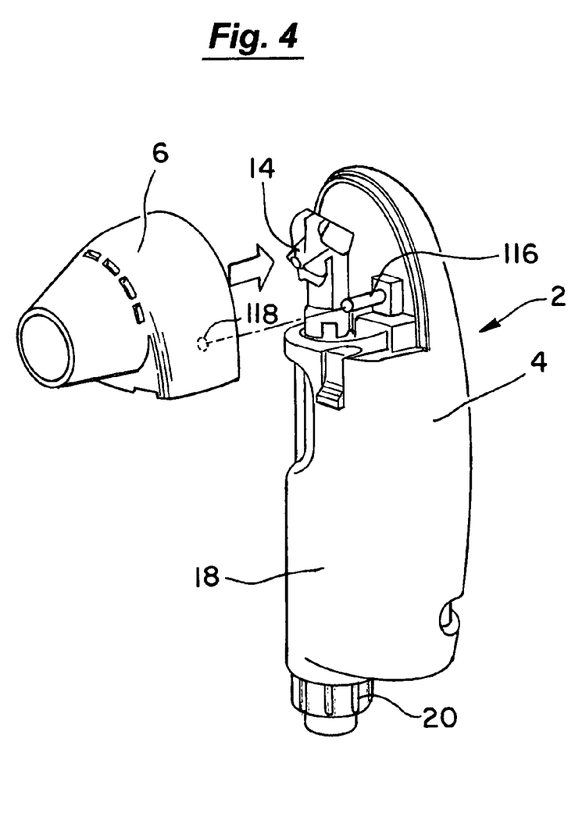
FIG. 4 shows the medicament assembly mounted to the aerosolizing device with the mouthpiece removed.

The container 12 and reservoir 14 form a medicament assembly 48. The container 12 is preferably mounted to the reservoir 14 by the user immediately before loading the container 12 and reservoir 14. Alternatively, the container 12 and reservoir 14 may be loaded sequentially. For example, the container 12 could be mounted to the device 2 followed by mounting the reservoir 14 to the container 12. The medicament assembly 48 may also be provided as a single unit that the user replaces all at once.

The reservoir 14 has an opening 50 that delivers the medicament to the aerosol generator 8. The opening 50 is oriented to form a feed angle of about 5-30°, and may be about 15°, relative to the longitudinal axis L of the container 12 as defined by the container body. The opening 50 also may have a diameter of about 0.05-0.25 inches and may be about 0.15 inches. The opening size and feed angle provide smooth delivery of the medicament from the reservoir 14 to the aerosol generator 8 particularly when the aerosol generator is oriented somewhat upright.

The medicament travels along a medicament path 52 between the container 12 and reservoir 14. The medicament path 52 includes the needle 40 and a channel leading from the needle 40 to the reservoir 14. The medicament path 52 may, of course, be formed in any other manner, including as a simple lumen or tube extending between the container 12 and reservoir 14. Furthermore, the medicament coupling between the container 12 and reservoir 14 may be any other suitable coupling other than the needle 40.

The medicament path 52 also includes a valve 54 that prevents contamination of the container 12. The valve 54 eliminates the need to pierce the container 12 a number of times as may be necessary to maintain sterility if the valve were not provided. The valve 54 may be a one-way valve such as a slit valve, ball valve, or duckbill valve. The valve 54 may be positioned to protect the entire medicament path between the container 12 and reservoir 14. To this end, the valve 54 may be positioned at the end of the medicament path 52, such as at a wall 56 of the reservoir 14. The valve 54 may also be positioned at a relatively low hydrostatic position relative to the reservoir 14 such that less than 25% of the reservoir 14, and perhaps less than 10%, is positioned hydrostatically below the valve 54. In this manner, the residual medicament volume in the reservoir 14 may be reduced since the valve 54 position can reduce the wetted surface of the reservoir 14 as compared to a valve positioned to dispense the medicament at a higher position in the reservoir. Of course, the valve 54 may be positioned at an elevated position in the reservoir 14 without departing from the invention. The valve 54 may also direct the medicament at the aerosol generator 8. The valve 54 may direct a stream of medicament at the aerosol generator 8 so that air in the reservoir 14 near the aerosol generator 8 is actively removed. A problem that can occur when delivering medicament to the aerosol generator is that air can be trapped near the aerosol generator, which can inhibit proper functioning of the device. The orientation of the valve 54 and the ability of the valve 54 to deliver a stream of medicament together reduce the risk of trapping air around the aerosol generator 8.

The reservoir 14 has an inner wall 71 that has a tear-drop shape and is substantially free of corners, seams, and edges to encourage medicament drainage. The reservoir 14 has a back-wall 60 that forms an angle of about 20-70° with respect to horizontal when the device is held in a preferred operating orientation. The inner wall 62 of the reservoir 14 is also preferably hydrophobic, but may be hydrophilic, depending upon the application and particular medicament, to further reduce the residual volume. The reservoir 14 may also have a relatively small volume to minimize the surface area of the reservoir 14. The tear-drop shape, smooth interior wall, angled backwall 60, and hydrophobic surface all encourage liquid in the reservoir 14 to flow downward toward the aerosol generator 8, thereby minimizing the residual medicament volume.

The aerosol generator 8 may be angled away from the reservoir 14 at an angle of about 0-45° relative to vertical and may be about 15° when the device is in the preferred operating orientation. The reservoir 14 may be made in any suitable manner and with any suitable materials. For example, the reservoir 14 may be made out of polypropylene and formed by injection molding. The aerosol generator 8 may be oriented in any other manner and may be any type of aerosol generator.

The mouthpiece 6 may be removable to load and remove the container 12 and/or reservoir 14. Removal of the mouthpiece 6 also permits cleaning of the mouthpiece 6 and aerosol generator 8. The aerosol generator 8 may be cleaned or removed after each use or at any predetermined interval, such as, for example, after a predetermined number of containers 12 and/or reservoirs 14 have been used. The mouthpiece 6 or aerosol generator 8 may even be removed and replaced with each container 12 or assembly 48. The mouthpiece 6 may be mounted with a suitable connection, such as a snap-fit connection or latch with the rest of the housing. In one embodiment, the mouthpiece 6 includes separate medicament and air-flow passages so that the medicament particles are mixed with air in the user's mouth when the user inhales on the mouthpiece. This is described in further detail in connection with FIGS. 9A and 9B below.

Figure 10:
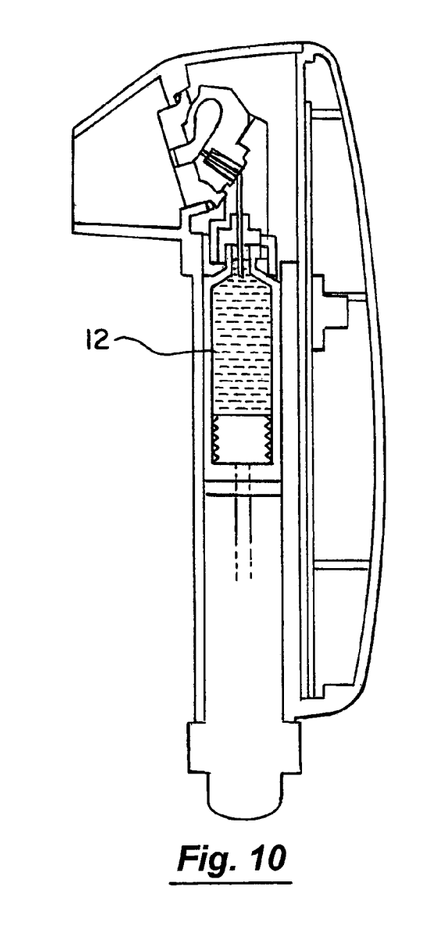
FIG. 10 is a cross-sectional view of the aerosolizing device with the reservoir empty.
Figure 11:
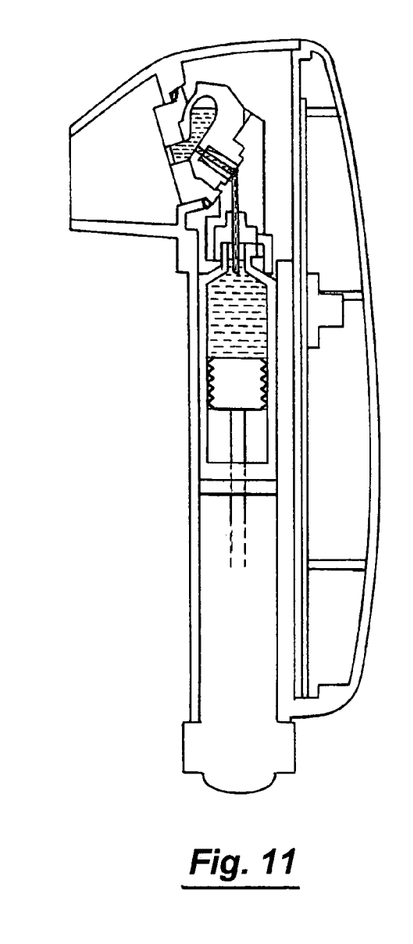
FIG. 11 is a cross-sectional view of the aerosolizing device with the reservoir filled with a volume of medicament.

The aerosol generator 8 may include a vibrating assembly 80. The vibrating assembly 80 includes a piezoelectric element 82 mounted to a substrate 84. The substrate 84 may be cup-shaped 86 or may have any other suitable shape, such as a flat ring or plate. A vibrating element 88 with a number of holes 90 is mounted to the substrate 84. The vibrating element 88 is preferably dome-shaped and the holes 90 may be tapered. The vibrating element 88 and assembly 80 may, of course, be any other suitable element, such as a flat plate, thin mesh, or flexible membrane, without departing from the scope of the invention. Furthermore, various aspects of the invention may be practiced independent of the particular aerosolizing method and device.

The substrate 84 is coupled to the mouthpiece directly or by a mounting element 92, which secures the vibrating assembly 80 to the housing 4 and specifically the mouthpiece 6. The vibrating assembly 80, via the mounting element 92, is coupled to the housing 4 by a flexible connection 94, such as a resilient connection 95. The connection 94 may be formed in part by a spring, foam, or elastomeric element disposed between the vibrating assembly 80 and housing 4. In the particular embodiment shown, an elastomeric element 96 having an oval cross section is shown, although a C-shaped, U-shaped, or other suitably shaped cross-section may be used. The flexible or resilient connection 94 can reduce dampening of the vibrating assembly as compared to rigid connections with the mouthpiece or housing 6.

The resilient connection 95 also provides a modest closing force on a medicament seal 98 between the aerosol generator 8 and reservoir 14. The closing force created by the resilient connection 95 helps to prevent medicament from leaking out of the seal 98 between the reservoir 14 and aerosol generator 8. The seal 98 is formed by a sealing element 100, such as an O-ring, on the mounting element 92, and a complementary sealing element 102, such as a groove on the reservoir 14. The connection 94 naturally biases the sealing elements 100 and 102 together in that the connection 94 is slightly compressed when the reservoir 14 is mounted. The proper alignment of the reservoir 14 is achieved when the mouthpiece 6 registers with the rest of the housing 4.

The mounting element 92 may also engage the vibrating assembly 80, such as the vibrating element 88, and direct medicament to the vibrating element 88. The mounting element 92 may engage the vibrating element 88 with any suitable connection. For example, the mounting element may be glued to the vibrating element 88 or may have an O-ring that engages the vibrating element. As mentioned above, the vibrating element is generally oriented within 45° of vertical, and preferably about 15°, during operation, but may be oriented at any other angle without departing from the invention.

The device 2 is preferably breath-actuated in any suitable manner. In one embodiment, a pressure sensor 110, such as a pressure transducer 112, measures pressure in the mouthpiece chamber 114 so that when the user inhales on the mouthpiece 6, the sensor 110 detects the pressure drop and triggers the aerosol generator 8 at a trigger pressure. The pressure sensor 110 may be mounted to the mouthpiece 6 or may be mounted to the body of the device 2. A pressure-sensing conduit 116 extends to a rear chamber 118 of the device 2 where the pressure sensor 110 is mounted. A pressure-sensing port 118 in the mouthpiece 6 receives the conduit 116 to provide pressure communication between the mouthpiece chamber 63 and pressure sensor 110 via the conduit 116.

Figure 9A:
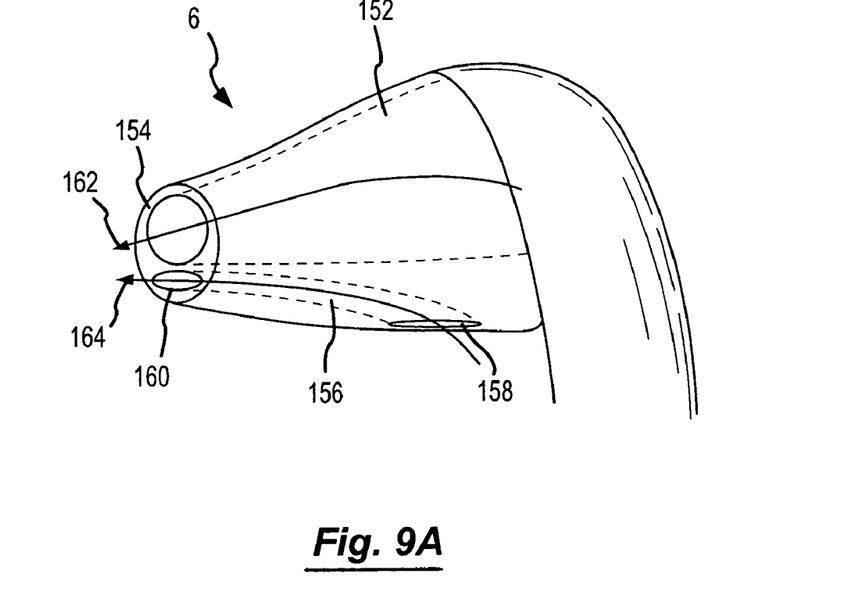
FIGS. 9A and 9B are respectively show perspective and cross-sectional views of a mouthpiece in another embodiment.
Figure 9B:
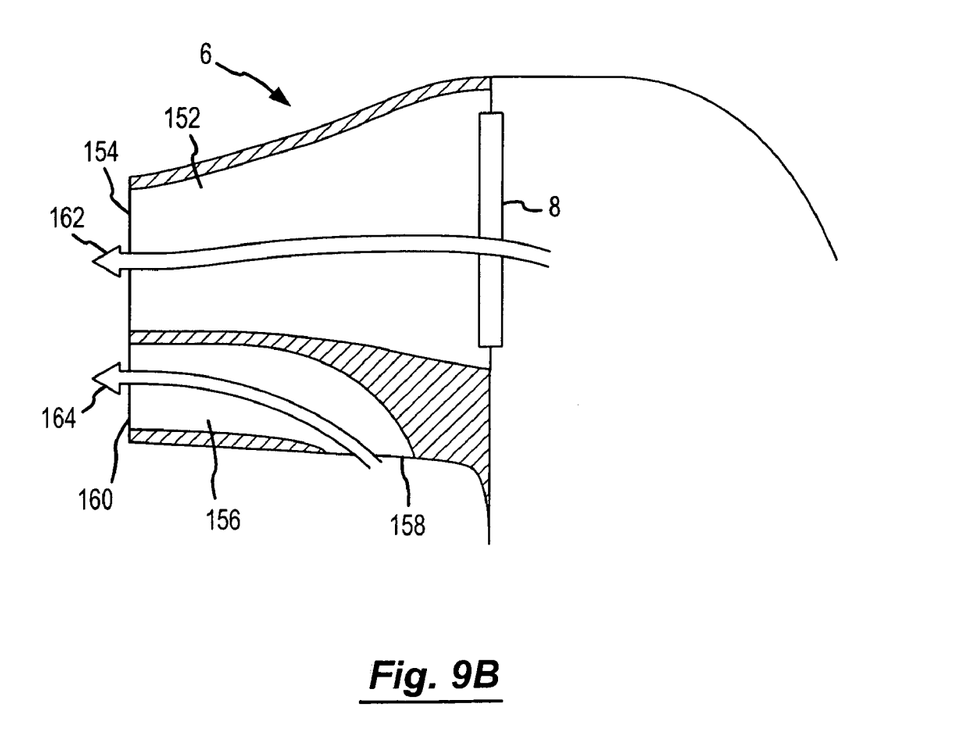

An embodiment for the mouthpiece is shown with the perspective and cross-sectional views of FIGS. 9A and 9B. In this embodiment, the mouthpiece 6 is designed to cause mixture of medicament particles with air in the mouth and upper respiratory tract of the patient, rather than mixing them in the device and transferring the mixture to the patient's mouth. Mixture of particles and air in the mouth and upper respiratory tract of the patient in this way reduces the interaction of particles with internal surfaces of the device, and consequently reduces particle coalescence to increase the respirable fraction of particles delivered to the lungs.

This is accomplished in the illustrated embodiment by providing separate flow passages for the medicament and for mixing air. Referring collectively to FIGS. 9A and 9B, the mouthpiece 6 comprises a hollow body that defines a medicament-flow passage 152 and an air-flow passage 156. The aerosol generator 8 is positioned such that medicament particles stream from the aerosol generator 8 through the medicament-flow passage 152 to a mouthpiece opening 154 in response to a pressure drop at the mouthpiece opening 154. Such a pressure drop is typically provided by a patient inhaling at the end of the mouthpiece, thereby also providing a pressure drop at an outlet opening 160 of the air-flow passage 156. An inlet opening 158 to the air-flow passage 156 is provided in communication with ambient atmosphere to provide a source of air for mixing with the medicament particles. While the aerosol generator 8 is shown comprised by the mouthpiece 6, it may in other embodiments be installed in other parts of the inhalation device as described above.

The flows of medicament and air are respectively shown with arrows 162 and 164. A number of tests have been performed to assess the effectiveness of the mouthpiece 6 shown in FIGS. 9A and 9B. One conclusion from these tests is that, while the emitted dose of medicament is generally improved with the design, distribution of the medicament in a patient's mouth may be further improved if the outlet opening 160 of the air-flow passage 156 is below the mouthpiece opening 154 for the medicament when inserted into a patient's mouth. While other orientations may be used in some embodiments, there is a tendency for the medicament to be driven against a patient's tongue if the relative position of the air-flow-passage outlet opening 160 is too high relative to the mouthpiece opening 154. Positioning the air-flow-passage outlet opening 160 below the mouthpiece opening 154 increases the path above the tongue. This minimizes oralpharyngeal deposition on the tongue, cheeks, and back of the patient's throat, thereby further improving delivery of medicament to the patient's lungs.

Figure 9C:
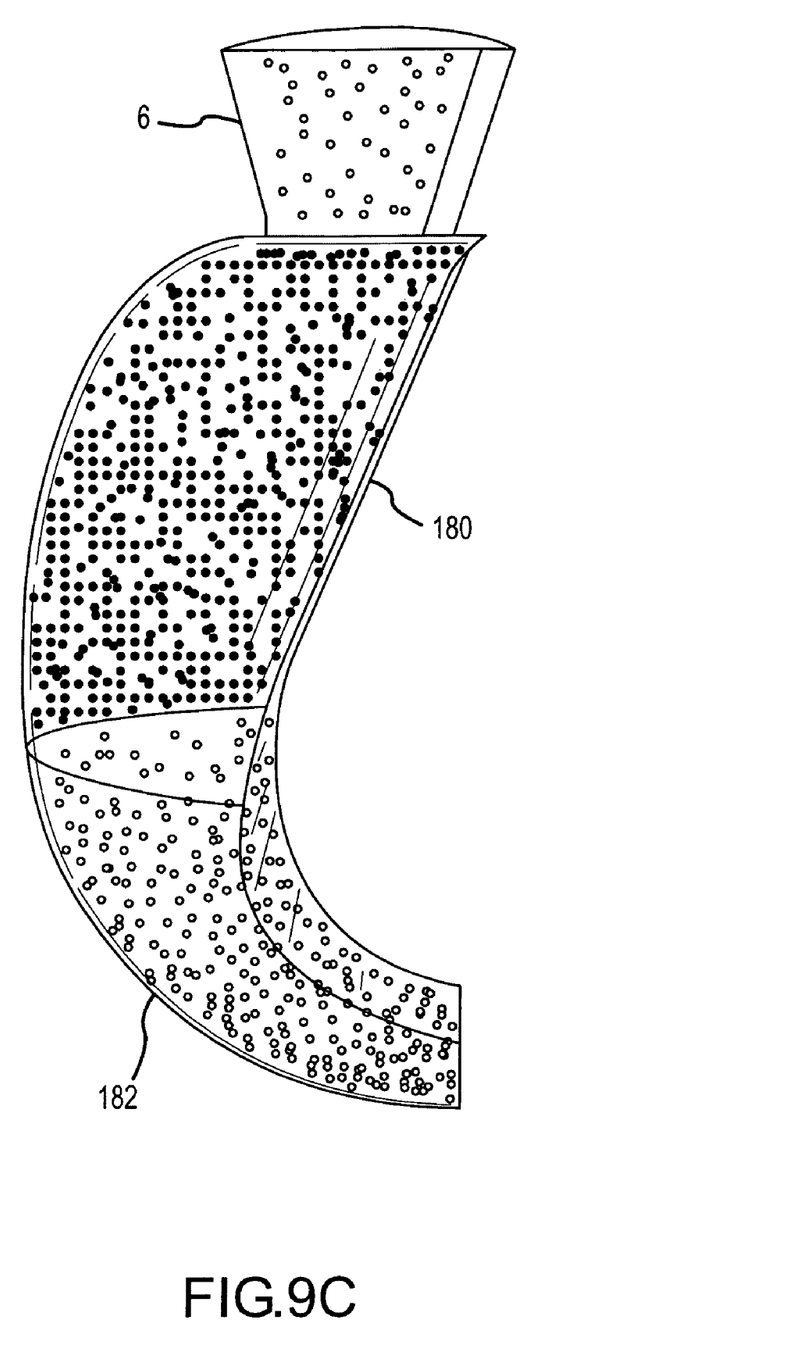
FIG. 9C provides results of a simulation illustrating flows of medicament and air using the mouthpiece of FIGS. 9A and 9B.

FIG. 9C provides results of simulations that show the flow of air and medicament using the mouthpiece shown in FIGS. 9A and 9B. The figure shows the mouthpiece 6 and portions of a user's oralpharyngeal tract broadly separated into mouth 180 and pharynx 182. Flows of medicament and air from the mouthpiece 6 are shown with dots, with the dark dots corresponding to air and the lighter dots corresponding to medicament. The air flow is provided from the air-flow passage of the mouthpiece, at the bottom of the mouthpiece. As is evident from the drawing, this position for the air flow causes the air to act as a chaser source that mixes with the medicament and improves efficient flow of the medicament from the mouth to the pharynx and into the lungs. The initial flow of medicament from the medicament flow passage into the mouth may be provided by a propulsive mechanism of the aerosol generator as described above, causing the medicament to be ejected through the medicament flow passage. In this way, the absence of mixing air with medicament in the mouthpiece does not adversely affect delivery of the medicament.

Quantitative results of some of the tests are compared in Tables 1a and 1b. Table 1a provides results for a hand-held inhalation device having a vented mouthpiece to provide mixing of aerosolized liquid particles with air in the mouthpiece. Table 1b provides corresponding results for a hand-held inhalation device like the one shown in FIGS. 9A and 9B that causes such mixing in the patient's mouth. The design of the inhalation device used in the tests was otherwise identical for both sets of trials.

TABLE 1a

Results Using Vented Mouthpiece

| Flow Rate (L/min) | Medicament Volume (µL) | Emitted Dose (%) | Average Emitted Dose (%) | Standard Deviation (%) |
|---|---|---|---|---|
| 28.3 | 200 | 80.1 | 78.2 | 2.2 |
|  |  | 75.8 |  |  |
|  |  | 78.7 |  |  |
| 60 | 200 | 77.3 | 71.9 | 5.3 |
|  |  | 66.6 |  |  |
|  |  | 71.8 |  |  |

TABLE 1b

Results Using Mouthpiece with Separate Medicament and Air Flows

| Flow Rate (L/min) | Medicament Volume (µL) | Emitted Dose (%) | Average Emitted Dose (%) | Standard Deviation (%) |
|---|---|---|---|---|
| 28.3 | 200 | 96.1 | 96.1 | 0.5 |
|  |  | 95.5 |  |  |
|  |  | 96.6 |  |  |
| 60 | 200 | 92.2 | 94.3 | 2.2 |
|  |  | 97.9 |  |  |
|  |  | 93.4 |  |  |
|  |  | 93.8 |  |  |
|  |  | 94.2 |  |  |

For each mouthpiece, trials were performed using flow rates of 28.3 L/min and 60 L/min, all with a medicament volume of 200 µL. The amount of medicament leaving the mouthpiece was measured, with the emitted dose being defined as the percentage of medicament leaving the mouthpiece to the total medicament volume of 200%. For the vented mouthpiece, the average emitted dose was 78.2% for the lower flow rate and 71.9% for the higher flow rate. At both flow rates, the average emitted dose was higher with the mouthpiece described in connection with FIGS. 9A and 9B, being 96.1% at the lower flow rate and 94.3% at the higher flow rate. The standard deviations for the results are noted in the tables, from which it is generally evident that higher emitted doses are produced with less variability at lower flow rates for both mouthpieces.

Operation of the device is now fully described. The user detaches the mouthpiece and loads the medicament assembly into the device. The medicament assembly may be formed by the container and reservoir, which are attached together by the user or mounted in sequence to the device. Once the container and reservoir are attached together, the interlocking feature may prevent disassembly and thus prevent improper usage of the device and parts thereof. The device may be primed in any suitable manner. For example, a volume of medicament equal to or just larger than the medicament path may be delivered when the container is loaded or when the first dose is delivered from a particular container. Alternatively, medicament may simply by delivered from the container until medicament is sensed in the reservoir.

Figure 12:
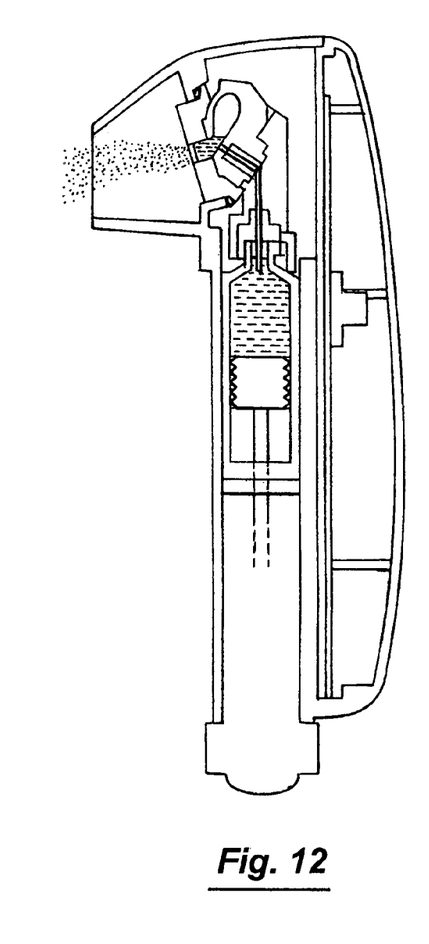
FIG. 12 shows the aerosol generator delivering the aerosolized medicament through the mouthpiece.

When the user is prepared to inhale the aerosolized medicament, the user operates the dosing controls to select and deliver a volume of medicament from the container to the reservoir. The dosing mechanism moves the piston to move medicament through the medicament path, out the valve and into the reservoir as shown in FIGS. 10 and 11, to produce a flow of aerosolized medicament as shown in FIG. 12. The user then operates the device by simply inhaling on the mouthpiece. When the user inhales, the pressure sensor detects the drop in pressure until the trigger pressure is reached, at which time the aerosol generator is activated. Medicament and air are separately drawn into the user's mouth where they mix. The device continues to aerosolize medicament while the user continues to inhale. This process is repeated until all of the solution has been aerosolized. The device may also measure, detect, or calculate when all of the medicament in the reservoir has been aerosolized in any suitable manner. For example, the device may deactivate the aerosol generator by measuring the resonant frequency of the vibrating element before medicament is delivered and deactivating the aerosol generator just before the dry resonant frequency is reached again.

The invention has been described with respect to various specific embodiments, but it can be appreciated that various modifications may be made without departing from the scope of the invention. For example, while the description above has focused on a specific implementation of an aerosolizing inhalation device, it will be appreciated that many components may be used in combination with a variety of alternative designs for inhalation devices. In particular, the mouthpiece described above with separate medicament and air flow passages may be used with numerous types of inhalation devices that include an aerosol generator for aerosolizing medicament. Advantages resulting from the separation of air and medicament flows so that mixing occurs in the user's mouth may be realized with any of a variety of alternative designs for inhalation devices.

What is claimed is:

1. An aerosolizing inhalation device for aerosolizing a medicament to be inhaled by a user, the aerosolizing inhalation device comprising:
    a housing;
    an aerosol generator contained within the housing;
    a medicament feed system to supply medicament to the aerosol generator; and
    a mouthpiece comprising:
        a medicament flow passage to provide aerosolized medicament from the aerosol generator to an outlet of the medicament flow passage; and
        an air flow passage separate from the medicament flow passage, the air flow passage having an inlet in fluid communication with an ambient atmosphere and an outlet,
        wherein the outlets of the medicament flow passage and air flow passage are provided at an end of the mouthpiece to provide separate simultaneous flows of medicament and ambient air that remain separate from each other until mixing in the user's mouth upon inhalation by the user at the end of the mouthpiece.

2. The aerosolizing inhalation device recited in claim 1 wherein the outlet of the air flow passage is disposed substantially below the outlet of the medicament flow passage when the mouthpiece is oriented for insertion into the user's mouth.

3. The aerosolizing inhalation device recited in claim 1 wherein greater than 90% of medicament provided to the aerosol generator by the medicament feed system is expelled through the outlet of the medicament flow passage.

4. The aerosolizing inhalation device recited in claim 1 further comprising an electrical connector that couples the mouthpiece electrically to the aerosol generator.

5. The aerosolizing inhalation device recited in claim 1 further comprising a pressure-measurement port disposed to measure a pressure within the medicament flow passage.

6. The aerosolizing inhalation device recited in claim 1 wherein the aerosol generator is mounted to the housing with a resilient connection.

7. The aerosolizing inhalation device recited in claim 1 wherein the aerosol generator includes a vibrating element with holes, the aerosolized medicament being emitted through the holes in the vibrating element when the vibrating element is vibrated.

8. The aerosolizing inhalation device recited in claim 7 wherein the vibrating element comprises:
    a front side leading to the medicament flow passage such that aerosolized medicament passing through the holes enters the medicament flow passage; and
    a back side that receives the medicament to be aerosolized.

9. The aerosolizing inhalation device recited in claim 1 wherein the medicament feed system comprises:
    a removable container holding a number of doses of medicament to be aerosolized; and
    a reservoir coupled with the housing and holding a volume of the medicament in contact with the aerosol generator, the reservoir being in fluid communication with the removable container to allow the volume of medicament to be delivered from the removable container to the reservoir.

10. The aerosolizing inhalation device recited in claim 9 wherein the medicament feed system further comprises a one-way valve positioned to regulate flow between the removable container and the reservoir.

11. The aerosolizing inhalation device recited in claim 1 wherein the mouthpiece is removable.

12. The aerosolizing inhalation device recited in claim 1 wherein the aerosolized medicament comprises aerosolized liquid 13. The aerosolizing inhalation device recited in claim 1 wherein the aerosolized medicament comprises aerosolized powder.

14. A method for providing aerosolized medicament to a patient, the method comprising:
    storing a volume of the medicament;
    aerosolizing the volume of the medicament and flowing the aerosolized medicament through a medicament flow passage into the patient's mouth; and
    simultaneously flowing air through an air flow passage separate from the medicament flow passage into the patient's mouth in response to inhalation by the patient, whereby the medicament and air do not mix prior to their entry into the patient's mouth.

15. The method recited in claim 14 wherein the air is flowed into the patient's mouth along a path substantially below a flow of the aerosolized medicament into the patient's mouth.

16. The method recited in claim 14 wherein greater than 90% of the volume of the medicament is expelled through the outlet of the medicament flow passage.

17. The method recited in claim 14 further comprising measuring a pressure within the medicament flow passage.

18. The method recited in claim 14 wherein aerosolizing the volume of the medicament comprises:
    supplying the volume of the medicament to a vibrating element with holes; and
    vibrating the vibrating element to emit the aerosolized medicament through the holes.

19. The method recited in claim 14 wherein the medicament comprises a liquid.

20. The method recited in claim 14 wherein the medicament comprises a powder.

* * * * *